(12) United States Patent
Bates

(10) Patent No.: US 7,131,331 B2
(45) Date of Patent: Nov. 7, 2006

(54) NON-DESTRUCTIVE TESTING APPARATUS

(75) Inventor: Daniel Bates, Coventry (GB)

(73) Assignee: Airbus UK Limited (GB)

( * ) Notice: Subject to any disclaimer, the term of this patent is extended or adjusted under 35 U.S.C. 154(b) by 106 days.

(21) Appl. No.: 10/380,409

(22) PCT Filed: Sep. 13, 2001

(86) PCT No.: PCT/GB01/04100

§ 371 (c)(1),
(2), (4) Date: Jul. 16, 2003

(87) PCT Pub. No.: WO02/23165

PCT Pub. Date: Mar. 21, 2002

(65) Prior Publication Data

US 2004/0050164 A1 Mar. 18, 2004

(30) Foreign Application Priority Data

Sep. 15, 1920 (GB) .................... 0022612.6

(51) Int. Cl.
*G01N 29/00* (2006.01)
*H01L 41/08* (2006.01)

(52) U.S. Cl. .................... 73/589; 73/602; 73/598; 310/334; 310/358

(58) Field of Classification Search ............... 73/589, 73/655, 657, 598, 602, 600; 250/341.6, 334; 310/334, 358
See application file for complete search history.

(56) References Cited

U.S. PATENT DOCUMENTS

| | | | | |
|---|---|---|---|---|
| 3,111,633 A | * | 11/1963 | Day | 332/119 |
| 3,401,333 A | * | 9/1968 | Thompson | 324/632 |
| 3,572,099 A | * | 3/1971 | Wieczorek | 73/602 |
| 3,933,381 A | * | 1/1976 | Schurman | 292/57 |
| 5,338,928 A | * | 8/1994 | Jamieson et al. | 250/227.21 |
| 6,000,844 A | * | 12/1999 | Cramer et al. | 374/5 |
| 6,236,049 B1 | * | 5/2001 | Thomas et al. | 250/341.6 |
| 6,236,146 B1 | * | 5/2001 | Cramer et al. | 310/366 |
| 6,399,948 B1 | * | 6/2002 | Thomas et al. | 250/341.6 |
| 6,476,541 B1 | * | 11/2002 | Smith et al. | 310/334 |
| 6,759,659 B1 | * | 7/2004 | Thomas et al. | 250/341.6 |
| 6,786,098 B1 | * | 9/2004 | Bates | 73/606 |
| 6,786,099 B1 | * | 9/2004 | Janik | 73/655 |
| 6,838,670 B1 | * | 1/2005 | Lewis et al. | 250/341.6 |
| 2004/0056200 A1 | * | 3/2004 | Rothenfusser et al. | 250/341.1 |

* cited by examiner

*Primary Examiner*—Hezron Williams
*Assistant Examiner*—Jacques Saint-Surin
(74) *Attorney, Agent, or Firm*—Barnes & Thornburg LLP

(57) ABSTRACT

Apparatus for non-destructively testing material to enable detection of any damage sites, comprising means for generating localized heating at any damage site in the material, and means for imaging the material to enable detection of any localized heating at the damage site.

15 Claims, 6 Drawing Sheets

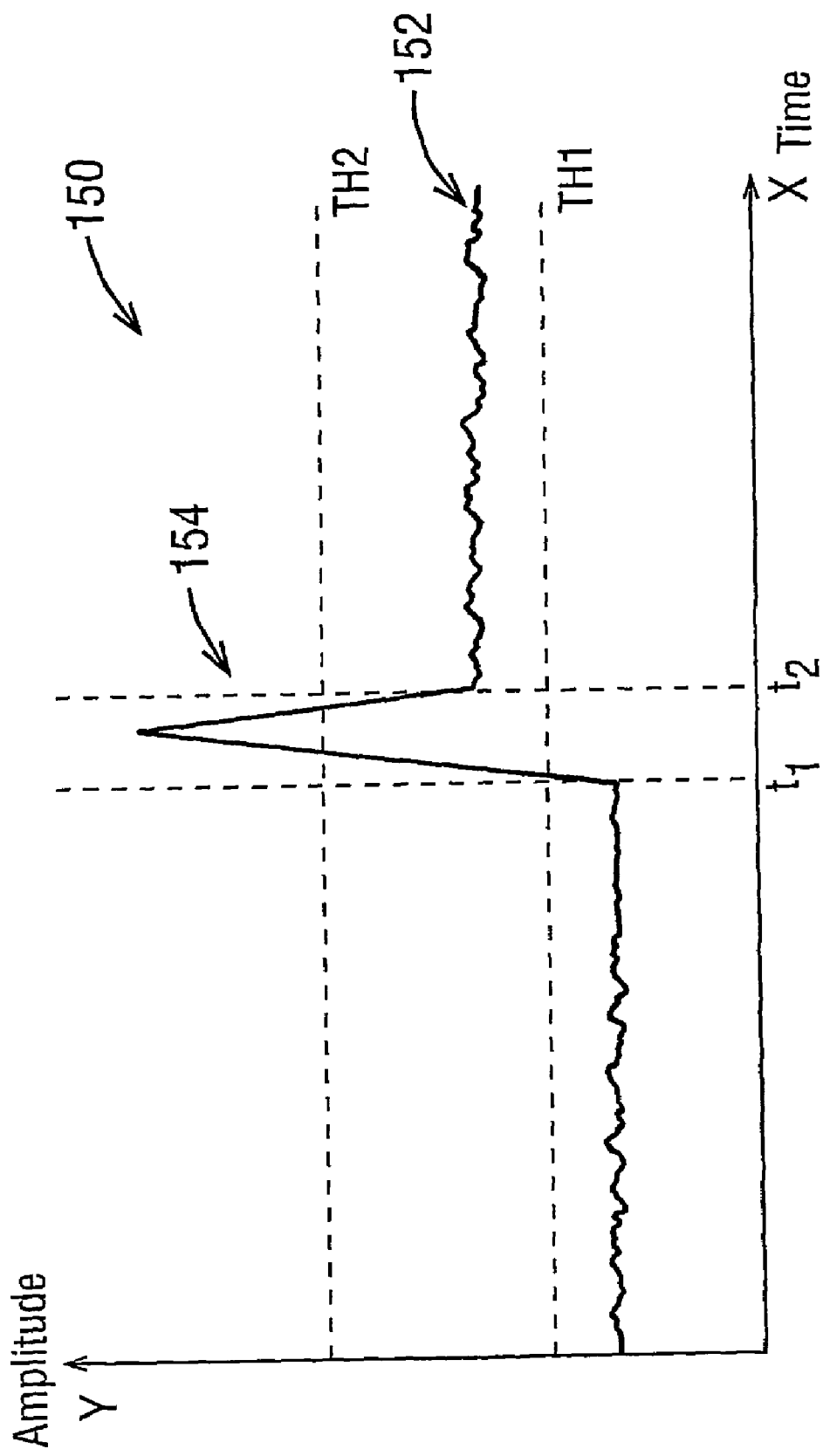

NON-DESTRUCTIVE TESTING APPARATUS

CROSS-REFERENCES TO RELATED APPLICATIONS

Figure 1:
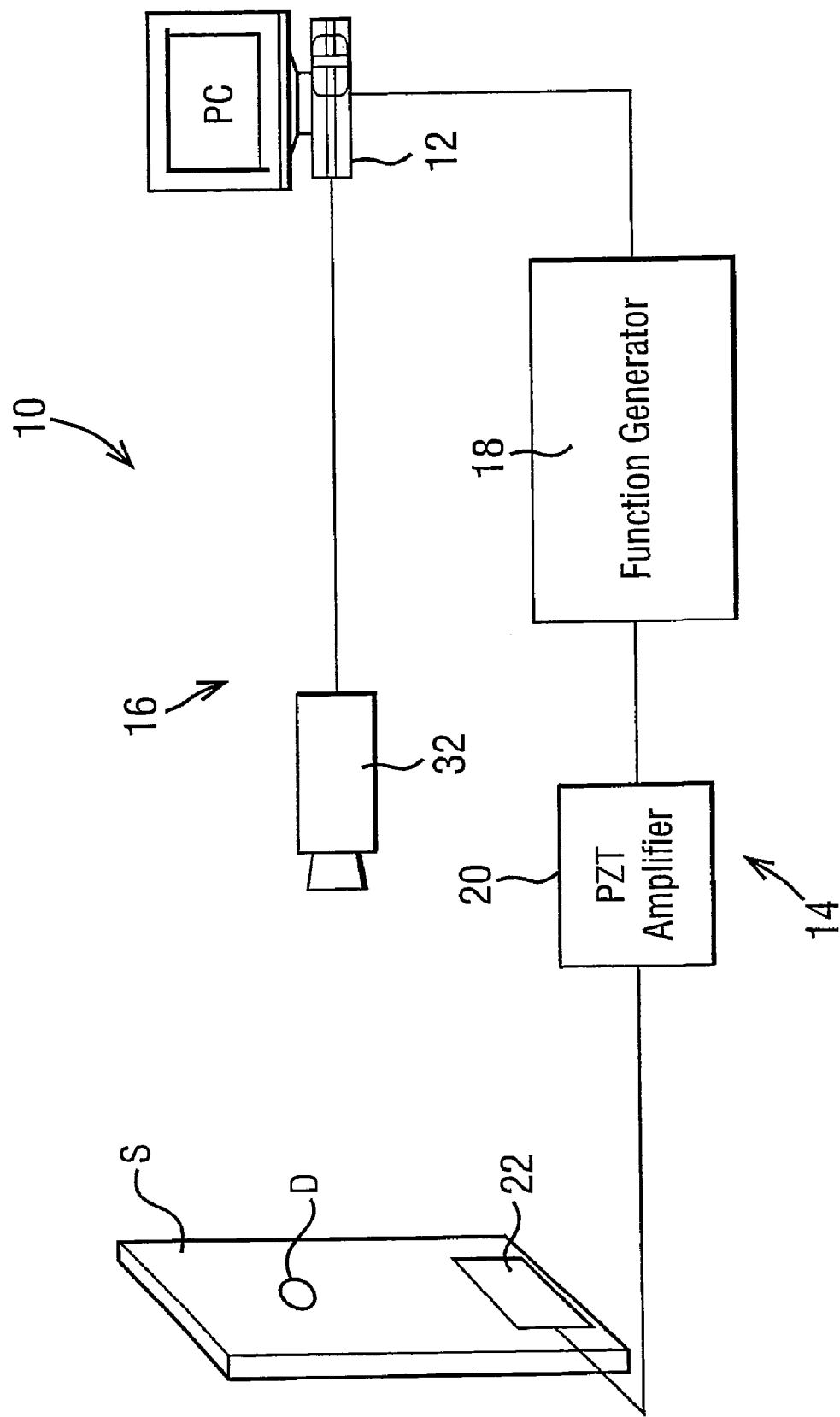

This application is a U.S. national application of international application serial No. PCT/GB01/04100 filed Sep. 13, 2001, which claims priority to Great Britain Patent Application No. 0022612.6 filed Sep. 15, 2000.

The invention relates to non-destructive testing apparatus and techniques and in particular to thermal non-destructive testing in order to detect barely visible impact damage (BVID). The invention is particularly, but not exclusively, directed to detecting such damage in compound materials as used on aircraft wing skins.

An object of the invention is to provide improvements in such apparatus and in particular to provide a relatively inexpensive, easy to operate system for non-destructive testing of materials. It is a particular object of the invention to provide a system which is locatable in position on a material in use, enabling relatively simple testing of material, thereby requiring minimal down time, for example of an aircraft being tested for barely visible impact damage on its composite wing skin structure.

One aspect of the invention provides apparatus for non-destructively testing material to enable detection of any damage site, comprising means for generating localised heating at any damage site and means for imaging the material to enable detection of any localised heating at a damage site.

Preferably the heating means comprises a piezo-electric actuator, and/or the actuator can be adapted to be bonded to the material or embedded within the material in use. Preferably a signal generator is provided operable to drive the piezo-electric actuator in use.

The piezo-electric actuator preferably comprises two regions of piezo-electric material. The two regions can comprise a stack of two pieces of piezo-electric wafers. The piezo-electric actuator can operably be driven in an extension mode, thereby to impact vibrations to the material in use. Preferably an array of piezo-electric actuators is mounted is provided which are adapted to be mounted on a material.

A signal generator which operatively drives the heating means is also preferably provided. The signal generator, preferably operably generates a frequency modulated signal. The frequency modulated signal can comprise a sine wave signal. The frequency modulated signal can comprise a phase-continuous frequency swept signal. Preferably the modulation is substantially linear. Also the carrier frequency is preferably in the range of about 1 to about 2000 Hz.

Preferably the carrier frequency is in the range of about 300 to 900 Hz, and/or in the range of about 550 to about 750 Hz. Preferably the modulation frequency of the carrier frequency range is between about 0.01 Hz and 1 Hz, and/or between about 0.1 and 0.3 Hz, and/or about 0.2 Hz.

Another aspect of the invention provides an array of piezo-electric actuators adapted to be mounted on a material to enable localised heating within the material at any damage sites. A further aspect of the invention provides material for use in sufficiently critical situations where damage sites in the material are required to be detected, which material comprises one or more piezo-electric actuators bonded to or embedded in the material operably to enable detection of any damage sites within the material. A further aspect of the invention provides apparatus for non-destructive testing material to enable detection of any damage sites in a substrate of material, comprising a signal generator which operably generates a frequency modulated signal for driving a piezo-electric actuator and means for detecting localised heating at a damage site, preferably comprising a thermal camera and controller such as a personal computer. Preferably an output from the signal generator is adapted to be connected to one or more piezoelectric actuators.

A further aspect of the invention provides apparatus for detecting impact damage comprising a piezo-electric actuator mounted on a substrate such as an aircraft wing skin, and a signal analyser operably connected to the piezoelectric actuator for detecting an acoustic signal indicative of impact on the substrate. Preferably an array of piezo-electric actuators is provided.

A further aspect of the invention provides impact damage detection apparatus comprising apparatus according to the first aspect of the invention and the last aspect.

Also an aspect of the invention provides an array of two or more piezo-electric actuators operably in communication with a connector enabling communication with real time impact damage detection apparatus.

Figure 2:
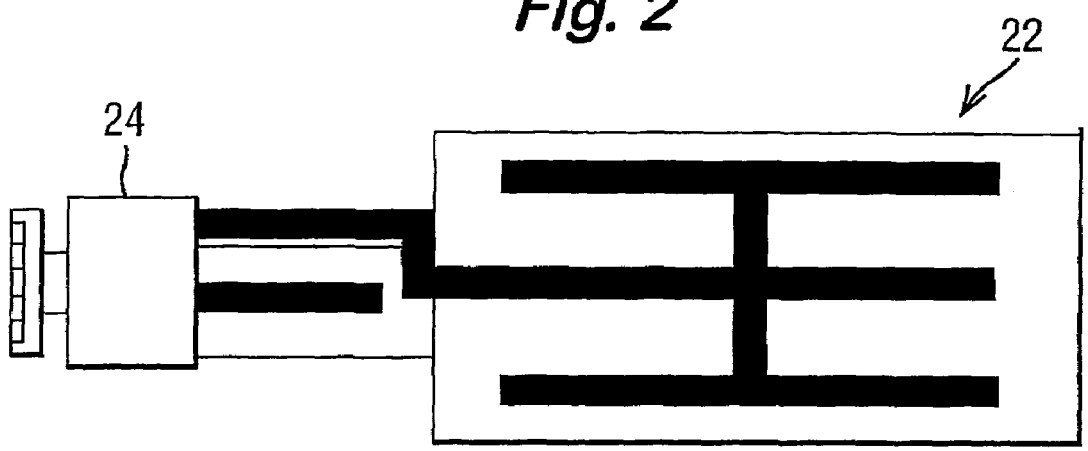
Figure 3:
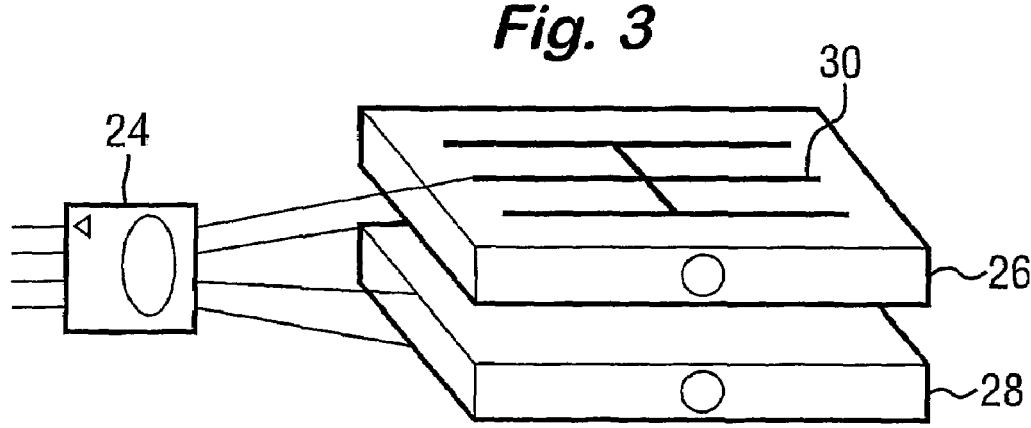
Figure 4:
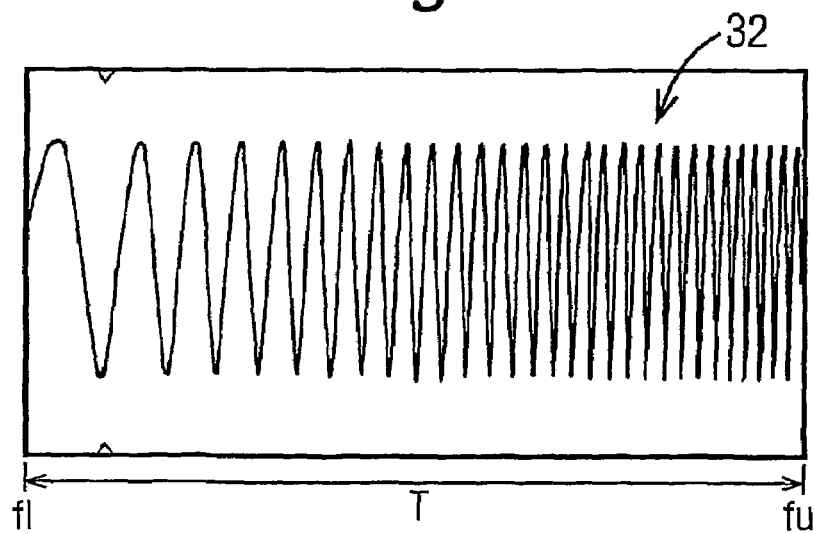
Figure 5:
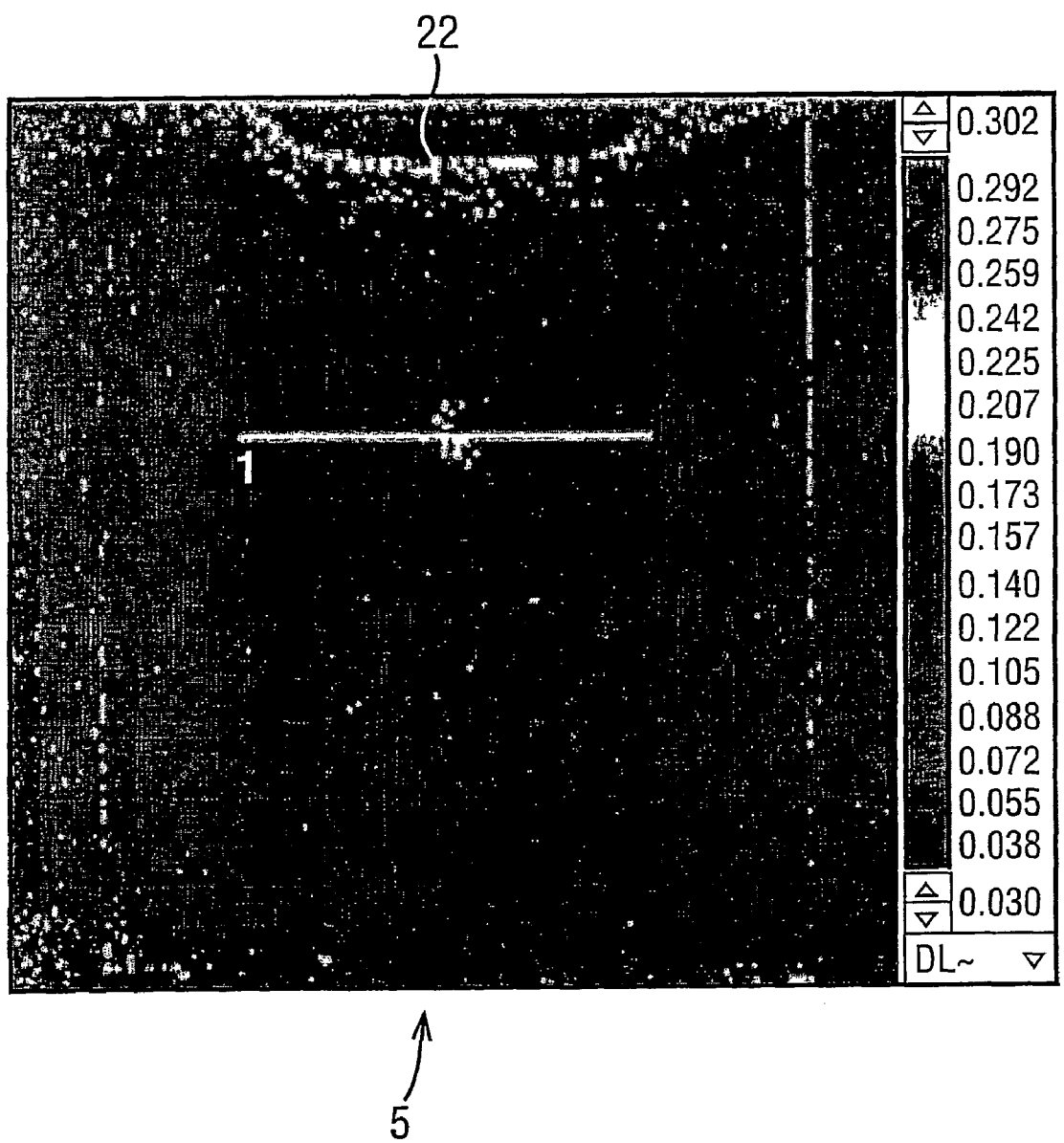
Figure 6:
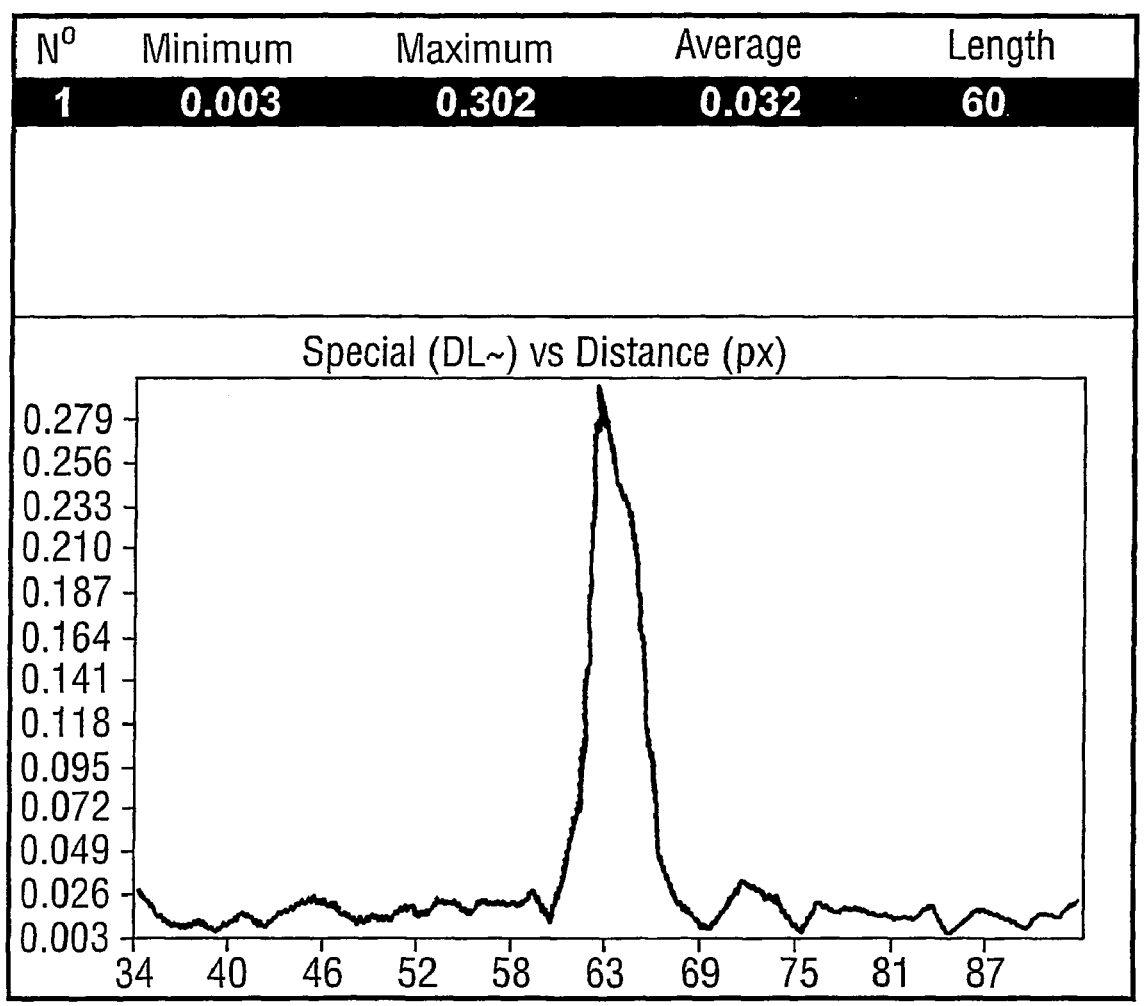

An embodiment of the invention will now be described, by way of example only, with reference to the accompanying drawings, in which:

FIG. 1 is a schematic block diagram of apparatus according to the invention, FIG. 2 is a plan view of a piezo-electric actuator forming part of the apparatus shown in FIG. 1, FIG. 3 is an exclamatic perspective view of the actuator shown in FIG. 2, FIG. 4 is an exclamatic diagram of part of the signal used to drive the actuator, FIG. 5 an introduction of an image captured using the apparatus shown in FIG. 1, FIG. 6 is a graph of the signal amipitute along line one shown in the image in FIG. 5.

Figure 7:
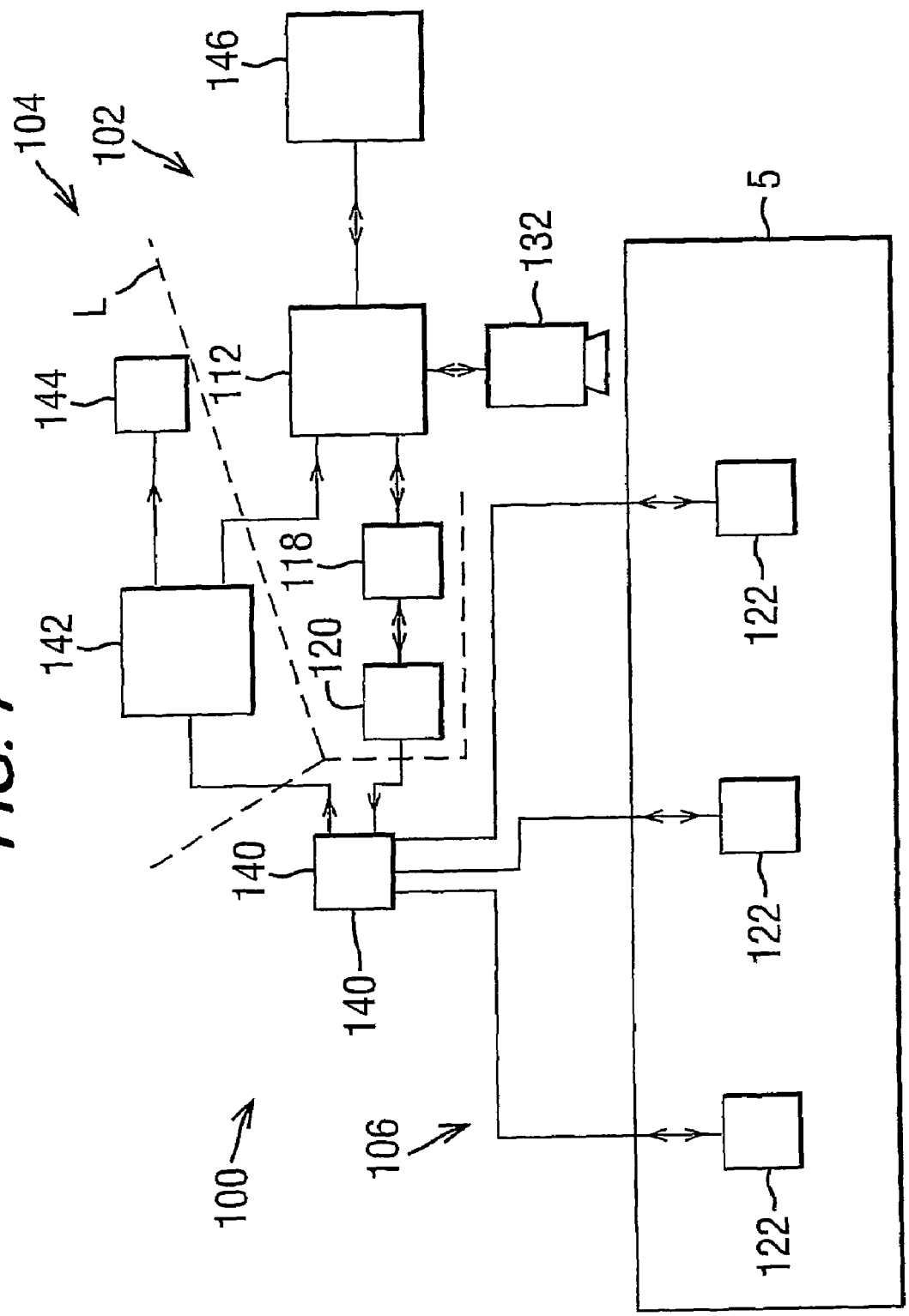

FIG. 7 is a schematic block diagram of a second embodiment of apparatus according to the invention, and FIG. 8 is a schematic graph illustrating real time detection of impact damage during a flight using the apparatus shown in FIG. 7.

Referring to FIG. 1 there is shown a non-destructive testing apparatus 10 according to the invention which comprises a computer 12, means 14 for causing localised heating within a substrate S and means 16 for imaging the substrate.

The heating means 14 can comprise a function generator 18 operably in communication with the computer 12. The function generator 18 drives an amplifier 20 which in turn generates a signal to piezo-electric actuator 22 attached to substrate S.

The function generator 18 oprerably produces a frequency modulated signal of the type described later in relation to FIG. 4. The output from function generator 18 is fed to piezo-electric amplifier 20 which amplifies the frequency modulated signal and drives piezo-electric actuator 22. Preferably the amplifier is capable of generating a signal in the order of 40 watts, such as a 200 (rms) volt, 0.2 amp signal.

The piezo-electric actuator 22 is shown in more detail in FIGS. 2 and 3. The specific actuator shown is one available from Active Control Experts of Cambridge, Mass., USA (ACX) and particularly their actuator QP20N. The particular device is a twin strip actuator comprising a stack of two piezo-electric wafers capable of a full scale strain extension in the order of 0.000264, and having a capacitance in the order of 0.12 micro Farads, and full scale voltage range of +/−200 volts. The twin layer structure is shown in the schematic exploded shown in FIG. 3 where two piezoelectric layers 26 and 28 are shown in a stacked arrangement. The actuator 22 further comprises an input 24 for connection to amplifier 20, and 4 electrodes 30, only the upper electrode of which is shown in FIG. 3. The actuator 22 can be moulded into or mounted onto a substrate S for example using an epoxy resin adhesive.

Referring back to FIG. 1, the imaging means 16 preferably comprises a thermal camera 32, connected to the computer 12. Camera 32 is preferably a thermal analysis camera capable of synchronised lock-in thermography. A suitable thermal camera 32 is available from CEDIP of Croissy-Beaubourg, France for example which comprises of a 128×128 focal plane array and stirling engine cooler.

The apparatus 10 is driven by computer 12 which can be a personal computer having user inputs such as a keyboard and mouse and user-display such as a video monitor, as well as input and output connections enabling synchronisation of actuation of the heating means 14 and imaging means 16, via communication lines such as appropriate wiring.

In use, computer 12 is used to synchronise operation of the piezo-electric actuator 22 and thermal camera 32 in order to optimise data capture by the camera. The data is stored and processed using computer 12 to enable analysis of images of the sample, thereby to enable detection of impact damage D within a sample. The system is adapted to enable detection of barely visible impact damage such as damage created by a six Joule impact on a composite structure such as an aircraft wing structure, forming substrate S.

In one preferred form, function generator 18 generates a frequency modulated signal 34 as shown in FIG. 4 which is preferably a phase continuous, linearly ramped signal as shown. The signal generated has a lower frequency SL and an upper frequency SU. The frequency is modulated substantially linearly, albeit incrementally such as in 1024 quantifiable steps, depending on the nature of the function generator 18, over a time period T. The carrier frequency of signal 34, is half the sum of the lower frequency and upper frequency, (FL+FU)/2, whereas the modulation frequency is the inverse of the time period (1/T.)

Preferably the appropriately amplified signal 34 is applied to piezo-electric actuator 22 by amplifier 20 over a predetermined period for data to be captured by camera 32 to enable detection of any damage sites such as barely visible impact damage D within a substrate S. In one form, a carrier frequency of 200 Hz is used with a modulation frequency in the order of 0.1 Hz and with an upper frequency in the order of 995 Hz.

Data capture by thermal camera 32 is preferably at a rate of 25 Hz for one complete image. Preferably 2500 images are captured and preferably 50 background images of the substrate prior to heating are used to enable background subtraction from the captured data images. In this example of the preferred embodiment the thermal image illustrated in FIG. 5 is, therefore, captured in 100 seconds. Preferably each image comprises 128×128 pixels according to the specification of thermal camera 32.

Referring to FIG. 5, there is shown an example of an output image as viewed on computer 12 from substrate S. FIG. 5 shows a lighter region at the top which represents the piezo-electric actuator 22 and has a lighter dot at its centre which is the position of damage site D shown FIG. 1. A horizontally line 1 is shown through the damage site. The individual data, such as digital level within the image, along line 1 is shown graphically in FIG. 6 where the signal is at a maximum at the damage site D. This represents the area of localised heating at the damage site D as observed by thermal camera 32.

Accordingly, the apparatus 10 enables qualitative analysis by a user to detect a damage site D by viewing results of images at the computer 12, and more accurately statistical analysis of data generated by the camera 32 in analysing data to detect a peak signal such as shown in FIG. 6.

The invention envisages composite structures such as aircraft wings, helicopter blades and so on having one or more piezo-electric actuators mounted or embedded therein, such that the actuator is capable of being coupled to apparatus 10 according to the invention. Beneficially, such an array of one or more piezo-electric actuators can be coupled to an on-board control system adapted to drive one or more actuators within the array as appropriate for the imaging means to enable detection of impact damage within the material. Beneficially, such an array of actuators coupled to a controller can provide a detection mechanism for monitoring impact damage on a real-time basis. For example, the actuators can be used as sensors to determine the existence of vibrations in an aircraft wing, thereby to detect large impact due to an electric signal generated by a piezo-electric actuator during use of an aircraft.

Referring to FIGS. 7 and 8, there is shown apparatus 100 which enables no destructive testing using apparatus 102 and separated by the dotted line L in FIG. 7. Apparatus 102 comprises substantial all those features shown in FIG. 1 where like components are given the same two digits reference prefix with the numeral 1. Accordingly, apparatus 1 and 2 comprises a computer 112, function generator 118, amplifier 120, and a thermal camera 132. Apparatus 102 further comprises a user interface 146 such as display, warning signals or similar devices.

Apparatus 100 further comprises an impact detector, apparatus 104 which can be integrated with apparatus 102 or independent thereof. Both apparatuses 102 and 104 are connectable to apparatus 106 comprises a connector 140 and an array of piezo-electric actuator 122 mounted in or attached to a substrate S such as an aircraft wing skin. Accordingly, an aircraft can comprise apparatus 106 wherein a wing skin has an array of piezo-electric actuators 122 mounted thereon which all communicate with connector 140 suitable located on the aircraft such as on its underside enabling connection to non-destructive testing apparatus 102 when the aircraft is on the ground or in a hanger for example, thereby to enable non-destructive testing using the technique describe in relation to apparatus 10.

Similarly, connector 140 is preferably suitably located for connection to the impact detector apparatus 104 which preferably enables real time collection of data and comprises a signal analyser 142 comprising for Example a suitable receiver, amplifier and microprocessor for analysing a signal from each of the piezo-electric actuators 122. The type of signal observed at analyser 142 is shown in FIG. 8. Signal 150 comprises an initial base line having a substantially equal amplitude over time. When an impact occurs near a piezo-electric actuator 122 this causes vibration at the piezo-electric actuator thereby to generate an electrical signal which is communicated to analyser 142 via connector 140. The signal comprises a pulse 154 over a time period t2 minus t1. The pulse 154 is seen as an increasing signal amplitude from a piezo-electric actuator 122 which passes through a first amplitude threshold level TH1 and subsequent second amplitude level TH2 before returning to a new baseline amplitude 152 between threshold TH1 and TH2. Accordingly, before the impact event at time t1 the piezo-electric actuator records acoustic emission below threshold level TH1. At time t1 the impact event occurs producing signal amplitude above threshold level TH2 which ends at time t2, after which a larger background threshold level 152 is recorded due to the continuous movement of impact damage material. By setting detection the threshold levels at the analyser 142 appropriately, an impact damage warning can therefore be giving by apparatus 104, for example in the aircraft cabin cockpit via a user interface 144 such as a warning light, or at a maintenance hanger, via a radio transmitter 144 to highlight potential problems with the structure so that repair crews can be ready when the aircraft lands. Analyser 142 can comprise memory for data from a flight which is communicable with computer 112 of apparatus 100 thereby to provide an overall apparatus which is capable of real time impact damage analysis and post impact damage analysis whereby computer 112 is configured to scrutinise more vigorously Sensibly those areas of substrate S local to an actuator 112 from which any actual or potential impact signals 154 have been observed.

The invention claimed is:

1. Apparatus for non-destructively testing material to enable detection of damage sites, comprising
    means for generating localised heating at a damage site in the material, comprising at least one piezo-electric actuator bonded to or embedded in said material,
    a signal generator for operatively driving said at least one piezo-electric actuator means, wherein the signal generator operably generates a frequency modulated signal, and means for detecting localised heating at a damage site, comprising a thermal camera means for imaging the material.

2. Apparatus according to claim 1 wherein each said piezo electric actuator comprises two regions of piezo-electric material.

3. Apparatus according to claim 2 wherein said two regions comprise a stack of two pieces of piezo-electric wafers.

4. Apparatus according to claim 1 comprising an array of piezo-electric actuators bonded to or embedded in a material.

5. Apparatus according to claim 1 wherein the frequency modulated signal comprises a sine wave signal.

6. Apparatus according to claim 5 wherein the frequency modulated signal comprises a phase-continuous frequency swept signal.

7. Apparatus according to claim 5 wherein the modulation is substantially linear.

8. Apparatus according to claim 5 wherein the carrier frequency of the frequency modulator signal is in the range of about 1 to 2000 Hz.

9. Apparatus according to claim 8 wherein the carrier frequency is in the range of about 300 to 900 Hz.

10. Apparatus according to claim 9 wherein the carrier frequency is in the range of about 550 to 750 Hz.

11. Apparatus according to claim 5 wherein the inverse of the period of modulation frequency of the carrier frequency range is between about 0.01 Hz and about 1 Hz.

12. Apparatus according to claim 11 wherein the modulation frequency is between about 0.1 and 0.3 Hz.

13. Apparatus according to claim 12 wherein the modulation frequency is about 0.2 Hz.

14. Apparatus according to claim 1, including an array of two or more piezo-electric actuators operably in communication with a connector enabling communication with real time impact damage detection apparatus.

15. Apparatus according to claim 1 wherein said material comprises aircraft wing skin.

* * * * *